Figure 1:
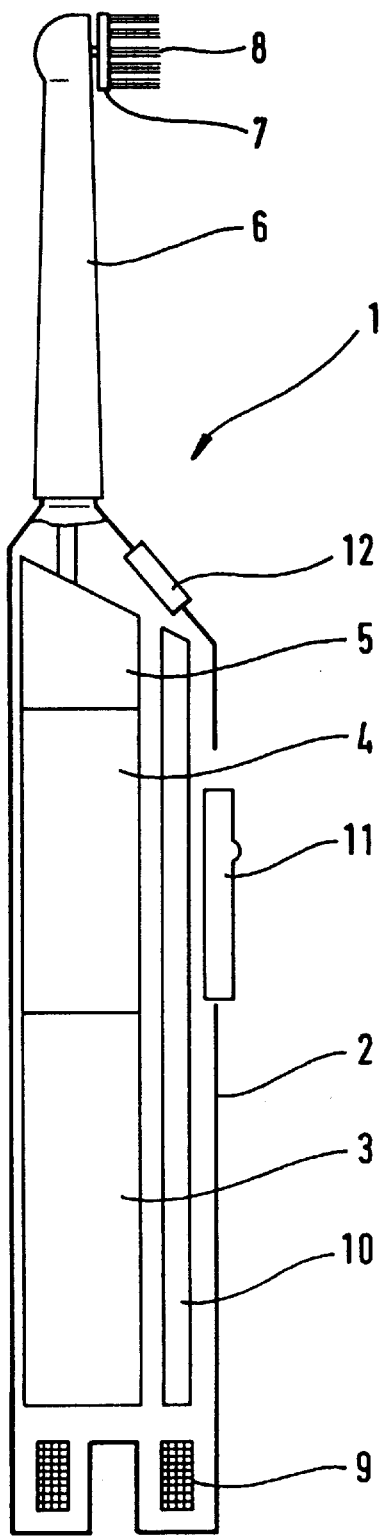

United States Patent

Hilfinger et al.

[11] Patent Number: 5,943,723
[45] Date of Patent: Aug. 31, 1999

[54] ELECTRIC TOOTHBRUSH

[75] Inventors: Peter Hilfinger, Bad Homburg; Philipp Jung, Darmstadt, both of Germany

[73] Assignee: Braun Aktiengesellschaft, Frankfurt, Germany

[21] Appl. No.: 09/067,885

[22] Filed: Apr. 28, 1998

Related U.S. Application Data

[63] Continuation of application No. PCT/EP96/04868, Nov. 7, 1996.

[30] Foreign Application Priority Data

Nov. 25, 1995 [DE] Germany ............................ 195 44 066

[51] Int. Cl.⁶ .................................................... A61C 17/34
[52] U.S. Cl. ................................ 15/22.1; 15/28; 15/105; 368/10
[58] Field of Search ..................................... 15/22.1, 22.2, 15/22.3, 22.4, 23, 28, 105, 167.1; 368/10

[56] References Cited

U.S. PATENT DOCUMENTS 4,450,599  5/1984  Scheller et al. ........................... 15/22.1
5,165,131 11/1992  Staar ......................................... 15/22.1
5,544,382  8/1996  Giuliani et al. ........................... 15/22.1

FOREIGN PATENT DOCUMENTS 0435329   7/1991  European Pat. Off. .
2918806  11/1980  Germany ............................... 15/167.1
3309687   9/1984  Germany .................................... 15/23
8610513 U  8/1986  Germany .
2250428   6/1992  United Kingdom .

*Primary Examiner*—Mark Spisich
*Attorney, Agent, or Firm*—Fish & Richardson P.C.

[57] ABSTRACT

The invention is directed to an electric toothbrush (1) in which a timing element (13) is provided whose purpose it is to indicate to a user the end of at least one cleaning period when the electric toothbrush (1) is activated. Still further, means (12) coupled to the timing element (13) are provided to enable the user to trigger the beginning (T4) of the cleaning period (PZD2). The effect thereby achieved is that the end (T2) of a cleaning period (PZD1) does not automatically start the beginning (T4) of the next cleaning period (PZD2), but that this particular beginning (T4) of the next cleaning period (PZD2) is freely selectable by the user.

6 Claims, 2 Drawing Sheets

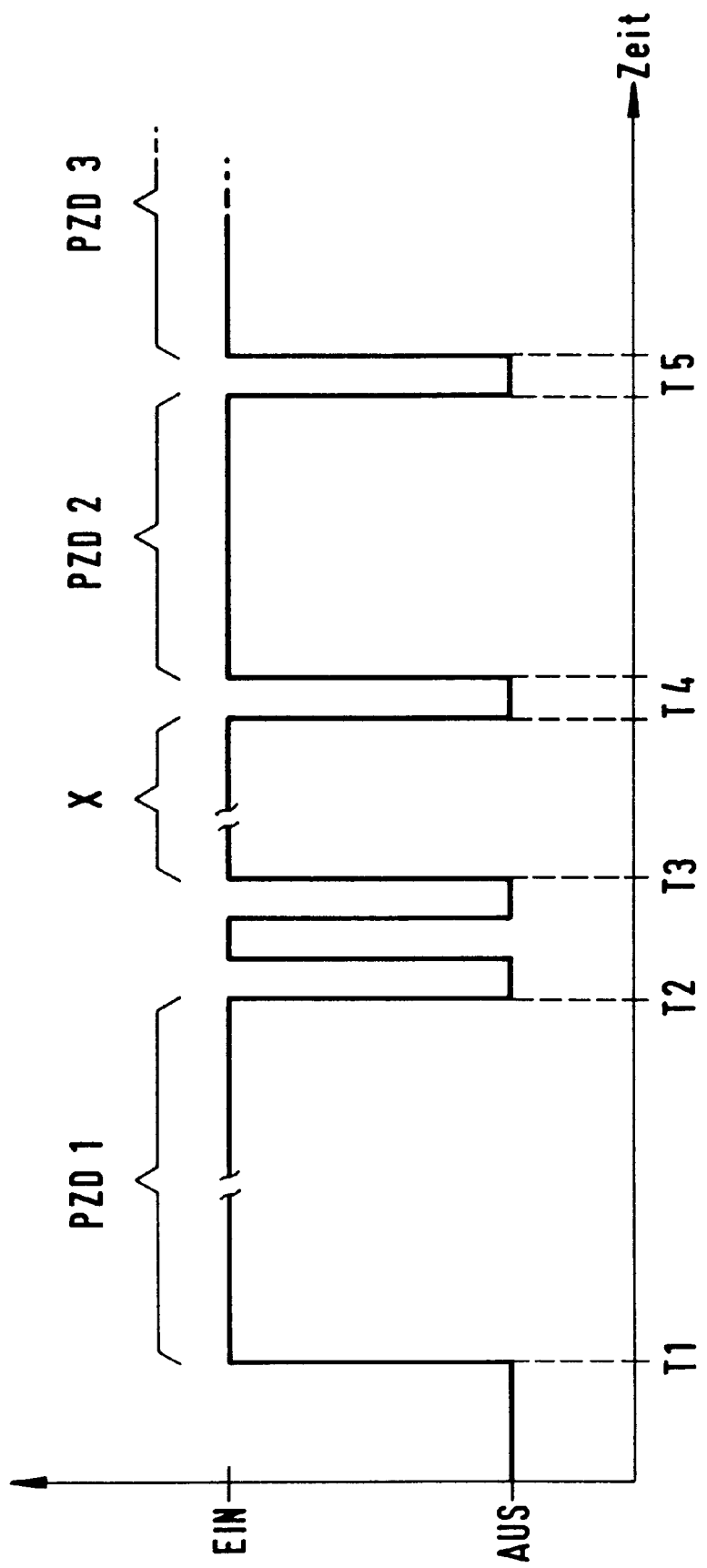

ELECTRIC TOOTHBRUSH

This is a continuation of International Application No. PCT/EP96/04868 filed Nov. 7, 1996 claiming priority from German Patent Application No. 19544066.8 filed Nov. 25, 1995.

This invention relates to an electric toothbrush with a timing element whose purpose it is to indicate to a user the end of at least one cleaning period when the electric toothbrush is activated.

An electric toothbrush of this type is known from German Offenlegungsschrift DE 33 09 687 A1. In this specification, an electric toothbrush has a time switch which after preset lengths of time delivers user-perceptible signals. This signal, which is issued after a cleaning period adequate for cleaning one dental quadrant or one specific dental section, for example, prompts the user to move on to the next quadrant or dental section. After the cleaning period allocated to this particular quadrant or dental section is over, another signal occurs indicating to the user that he should move on to the next quadrant or dental section. This process is repeated for all four quadrants or dental sections until all the user's teeth have been cleaned. With the durations of the cleaning period being the same for all quadrants or dental sections, this process should ensure that all the user's teeth are cleaned uniformly.

It has turned out, however, that the users of this process often lose track of the preset cleaning periods. For example, if a user is not yet finished with cleaning a dental section or quadrant although the corresponding signal has already indicated the end of the cleaning period allocated to this particular dental section or quadrant, the user will have to either move on to the next dental section or quadrant, in spite of not having completed the cleaning, or carry on cleaning with the result that the duration of the cleaning period for the next dental section or quadrant will be wrong. Hence in many cases it is not possible for the user's teeth to be cleaned uniformly.

It is an object of the present invention to provide an electric toothbrush that enables a user to clean all his dental sections or quadrants uniformly.

This object is accomplished with an electric toothbrush of the type initially referred to in that means coupled to the timing element are provided that enable the user to trigger the beginning of the cleaning period.

Hence when one cleaning period ends, the next cleaning period is not started automatically. The user is informed therefore that the cleaning period allocated to one quadrant is over but is not forced thereby to move on to the next quadrant. The term "quadrant" as used in the following is equivalent to the term "dental section". The user is thus free to finish cleaning his teeth in the present quadrant as he feels fit. Only then does the user move on to the next quadrant. He now triggers the beginning of the next cleaning period and starts to clean this next quadrant of his teeth. The user is no longer rushed, therefore, from one quadrant to the next by the successive cleaning periods but can decide for himself when he wants to move on to the next quadrant by triggering the next cleaning period. Hence there is no longer any danger of the user losing track of the successive cleaning periods for the various quadrants. The possibility of non-uniform cleaning of the various quadrants is thus also eliminated. Instead the user receives a signal informing him that the cleaning period of one quadrant has ended and can then move on individually to the next quadrant and start its cleaning period.

In an advantageous aspect of the present invention, the next cleaning period can be triggered by the user before the preceding cleaning period ends. The user thus has the liberty of not being forced to wait for the particular cleaning period to end. Instead he can move on earlier to the next quadrant of his teeth, trigger the beginning of the allocated cleaning period and start to clean this next quadrant. This enables the user to adapt individually the cleaning of his teeth, for example to gaps between the teeth in a particular quadrant with an accordingly shorter cleaning period.

In another advantageous aspect of the present invention, the first cleaning period is triggered automatically by switching on the electric toothbrush. Hence the user does not have to trigger the start of the first cleaning period himself but gets this done automatically by switching on the electric toothbrush. This does not amount to any restriction of the user's liberty because he will usually begin to clean his teeth when he switches on the electric toothbrush.

In an advantageous further aspect of the present invention, provision is made for an electric switching device, as for example a push-button, as a means for triggering the beginning of the cleaning period. Hence the user is provided not only with an on/off switch for the electric toothbrush but also with the electric switching device. With this device the user can trigger the various cleaning periods individually and hence—apart from the first cleaning period—independently of switching on the electric toothbrush.

In a further aspect of the present invention, the electric toothbrush is switched off and on briefly several times to indicate that the cleaning period has ended. The user of the electric toothbrush is not forced, therefore, to watch a visual indicator or the like but is informed directly by the electric toothbrush being switched off and on briefly several times that the respective cleaning period is over. These brief interruptions to the operation of the electric toothbrush are bound to be noticed by the user without any essential impairment to the cleaning of the teeth.

Figure 2:
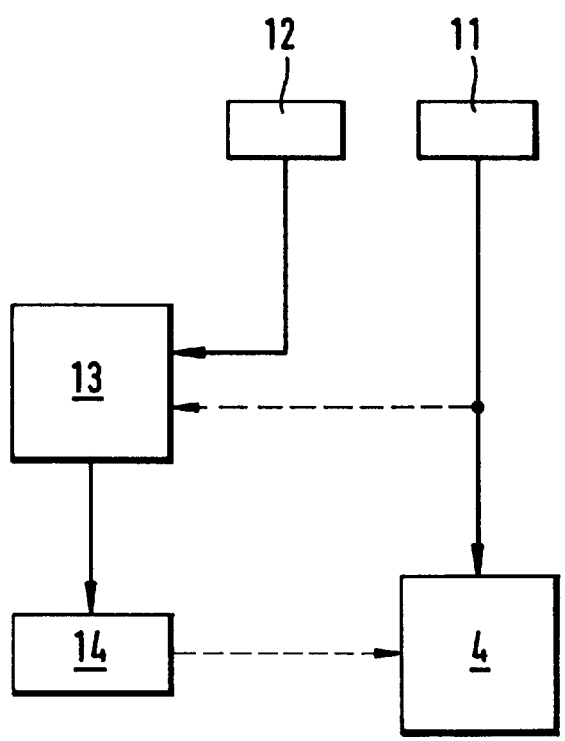

Further features, advantages and application possibilities of the present invention will become apparent from the subsequent description of embodiments illustrated in more detail in the accompanying drawings. It will be understood that any single feature and any combination of single features described and/or represented by illustration form the subject-matter of the present invention, irrespective of their summary in the claims and their back-reference. In the drawings, FIG. 1 is a schematic illustration of an electric toothbrush of the present invention;

FIG. 2 is a schematic block diagram representing components of the electric toothbrush of FIG. 1; and FIG. 3 is a schematic time diagram illustrating the operating states of the electric toothbrush of FIG. 1.

FIG. 1 shows an electric toothbrush 1 in which a storage battery 3, a motor 4 and a gearing 5 are accommodated in a housing 2. A brush attachment 6 carrying a bristle carrier 7 with projecting bristles 8 is attached to a free end of the electric toothbrush 1. When the electric toothbrush 1 is switched on, this bristle carrier 7 is set in motion, particularly a rotary motion, about an axis approximately parallel to the bristles 8 of the bristle carrier 7, by the motor 4 acting via the gearing 5.

A coil 9 and a printed circuit board 10 are also accommodated in the housing 2 of the electric toothbrush 1. The coil 9 serves the purpose of charging the storage battery 3, and electronic components required to operate the electric toothbrush 1 are mounted on the printed circuit board 10.

An on/off switch 11 and a push-button 12 are provided in the wall of the housing 2 where they are accessible from outside. A user can use the on/off switch 11 to switch on the electric toothbrush 1 and switch it off again. The push-button 12 represents very generally the means with which the beginning of a cleaning period can be triggered by the user, as will be explained in more detail below. This means does not necessarily have to be the push-button 12 as it is also possible in general to provide some other electric switching device such as a reed contact, a light barrier or the like.

The motor 4, the on/off switch 11 and the push-button 12 are shown in FIG. 2 in block form. A timing element 13 and an indicating device 14 are also provided. The on/off switch 11 is connected to the motor 4 so that a user is able to switch the motor 4 on and off by means of the on/off switch as already mentioned. The push-button 12 acts on the timing element 13 which is connected in turn to the indicating device 14. It is possible furthermore for the on/off switch 11 to act likewise on the timing element 13 and/or for the indicating device 14 to be connected to the motor 4.

The mode of operation of the electric toothbrush 1 will be explained in the following with reference to FIGS. 2 and 3. FIG. 3 presents a time diagram in which the activated (ON) and deactivated (OFF) operating state of the motor 4 of the electric toothbrush 1 is plotted over time.

At an instant of time T1, a user switches on the electric toothbrush 1 by means of the on/off switch 11. The bristle carrier 7 now performs the rotary motion initially referred to and the user can clean his teeth, beginning accordingly to clean the teeth of a first quadrant.

When the motor 4 is switched on, the timing element 13 begins to run as well. To enable this to take place automatically and simultaneously there has to be a connection between the on/off switch 11 and the timing element 13 as previously mentioned. In this way a first cleaning period PZD1 is then triggered automatically as of the instant of time T1 by switching on the motor 4.

Alternatively the possibility exists to have no connection between the on/off switch 11 and the timing element 13 so that the user himself has to start the timing element 13 by means of the push-button 12. In this case it is possible for the instant of time when the motor 4 is switched on to precede the instant of time when the timing element 13 begins to run.

After a preset cleaning period, particularly after a cleaning period of about 30 seconds, the timing element 13 indicates that the cleaning period for the current quadrant is over and the user can move on to clean the next quadrant of his teeth.

This indication that the cleaning period is over may be a visual or audible indication or occur in some other way. In these cases there is no need to connect the indicating device 14 to the motor 4.

It is possible in particular to indicate that the cleaning period PZD1 is over by switching the motor 4 off and on briefly several times. This is represented in FIG. 3 by the double switching off and on of the motor 4 in the period between the instants of time T2 and T3. For this type of indication to be possible there has to be a connection between the indicating device 14 and the motor 4 as referred to in the foregoing.

The end of the cleaning period PZD1 is only indicated by the timing element 13; the motor 4 remains activated and the cleaning period PZD2 for the next quadrant is not yet started. The user is thus completely free to decide for himself when actually to move from the current quadrant to the next quadrant without the cleaning period for the next quadrant being affected thereby. This is represented in FIG. 3 by a period X between the instants of time T3 and T4.

Once the user actually moves from the current quadrant to the next quadrant of his teeth, he actuates the push-button 12. In FIG. 3 this is the case at the instant of time T4. The timing element 13 thus starts the cleaning period PZD2 allocated to the second quadrant after the instant of time T4.

To confirm the beginning of the next cleaning period PZD2 it is possible for the timing element to deliver a visual, audible or other signal by means of the indicating device 14. It is also possible for the motor 4 to be switched off and on once, for example, as shown in FIG. 3.

The user may wish, for example, to move on to the next, that is, the third quadrant of his teeth before the cleaning period PZD2 has ended. This can be accomplished readily by the user using the push-button 12 to relay this changeover to the timing element 13, which then starts the next allocated cleaning period PZD3 before the preceding cleaning period PZD2 has ended. This is shown in FIG. 3 at the instant of time T5.

In this manner, all the user's dental quadrants are covered and cleaned uniformly. At the end of the complete dental cleaning operation it is possible for the timing element 13 to issue via the indicating device 14 an end signal different to those previously emitted.

We claim:

1. An electric toothbrush comprising:

a switch for activating the electric toothbrush;

a timing element capable of indicating at least two predetermined cleaning periods and of being triggered in response to an input from a user when the electric toothbrush is activated;

wherein a subsequent of the at least two cleaning periods can be triggered by the user independently of a preceding cleaning period while the electric toothbrush is activated.

2. The electric toothbrush as claimed in claim 1, wherein the subsequent cleaning period can be triggered by the user input before the preceding cleaning period ends.

3. The electric toothbrush as claimed in claim 1, wherein a first of the at least two cleaning periods is triggered automatically by switching on the electric tooth brush.

4. The electric toothbrush as claimed in claim 1, further comprising an electric switching device adapted to trigger a beginning of the at least two cleaning periods.

5. The electric toothbrush as claimed in claim 1, wherein the timing element causes the electric toothbrush to switch off and on briefly several times to indicate an end of a cleaning period.

6. The electric toothbrush as claimed in claim 4, wherein the electric switching device is a push-button switch.

* * * * *